(12) United States Patent
Connor

(10) Patent No.: US 9,572,717 B2
(45) Date of Patent: Feb. 21, 2017

(54) SHIELDED INTRAOCULAR PROBE FOR IMPROVED ILLUMINATION OR THERAPEUTIC APPLICATION OF LIGHT

(71) Applicant: Christopher Sheldon Connor, Hanover, NH (US)

(72) Inventor: Christopher Sheldon Connor, Hanover, NH (US)

( * ) Notice: Subject to any disclaimer, the term of this patent is extended or adjusted under 35 U.S.C. 154(b) by 320 days.

(21) Appl. No.: 13/892,558

(22) Filed: May 13, 2013

(65) Prior Publication Data

US 2014/0155870 A1 Jun. 5, 2014

Related U.S. Application Data

(63) Continuation of application No. 12/767,571, filed on Apr. 26, 2010, now Pat. No. 8,439,900, which is a
(Continued)

(51) Int. Cl.
*A61B 18/18* (2006.01)
*A61F 9/008* (2006.01)
(Continued)

(52) U.S. Cl.
CPC .............. *A61F 9/0084* (2013.01); *A61B 90/30* (2016.02); *A61F 9/008* (2013.01); *A61N 5/0601* (2013.01);
(Continued)

(58) Field of Classification Search
CPC ................... A61F 9/008; A61F 9/00736; A61F 2009/00861; A61F 2009/00863; A61F 2009/0087; A61F 2009/00872; A61F 2009/00887; A61F 2009/00889; A61F 2009/00891; A61F 2009/00893
(Continued)

(56) References Cited

U.S. PATENT DOCUMENTS 5,957,914 A * 9/1999 Cook ................... A61B 18/26
  606/10
7,141,048 B1 * 11/2006 Charles ............... A61F 9/00736
  604/264

(Continued)

*Primary Examiner* — Ahmed Farah
(74) *Attorney, Agent, or Firm* — Kurtz Firm, PLLC

(57) ABSTRACT

An intraocular light probe has a mask or shield affixed at its distal end thereof which forms a directed light beam for intraocular application of light to target tissues or intraocular application of therapeutic light. The mask or shield serves to more fully focus, intensify and direct the beam toward the target tissues. The mask or shield also helps direct light away from other tissues and away from the eyes of the surgeon. By placing a light probe beneath a surgical instrument such as a phacoemulsifier or vitrector, laser, cutting instrument (e.g., scissors or knife), forceps or probe/manipulator, whether as part of or separate from an infusion sleeve, a mask or shield effect is created. This has the same benefits of directing the beam toward target tissues, away from other tissues and away from the eyes of the surgeon. The mask/shield can be removed from the fiberoptic light for sterilization. The device of the invention is preferably introduced into the eye via the primary or side-port incision to provide intraocular cross-lighting of tissues during surgical procedures such as cataract surgery, corneal surgery, vitrectomy, intraocular lens implantation, refractive surgery, glaucoma surgery and vitreo/retinal surgery.

5 Claims, 3 Drawing Sheets

Related U.S. Application Data continuation of application No. 11/118,767, filed on May 2, 2005, now Pat. No. 7,704,246.

(60) Provisional application No. 60/566,619, filed on Apr. 30, 2004.

(51) Int. Cl.
 *A61N 5/06* (2006.01)
 *A61F 9/007* (2006.01)

(52) U.S. Cl.
 CPC ...... *A61B 2090/306* (2016.02); *A61F 9/00736* (2013.01)

(58) Field of Classification Search
 USPC .................................. 606/4, 6, 13–19, 107
 See application file for complete search history.

(56) References Cited

U.S. PATENT DOCUMENTS

| | | | |
|---|---|---|---|
| 7,704,246 B2* | 4/2010 | Connor | 606/6 |
| 8,439,900 B2* | 5/2013 | Connor | 606/6 |

* cited by examiner

SHIELDED INTRAOCULAR PROBE FOR IMPROVED ILLUMINATION OR THERAPEUTIC APPLICATION OF LIGHT

This application is a continuation of U.S. patent application Ser. No. 12/767,571 filed Apr. 26, 2010, which is a continuation of U.S. patent application Ser. No. 11/118,767 filed May 2, 2005, which claims priority to U.S. Provisional Patent Application No. 60/566,619 filed Apr. 30, 2004, the entire disclosures of which are incorporated herein by reference.

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD OF THE INVENTION

The present invention relates in general to the field of surgical instruments, and in particular to a shielded intraocular probe for insertion into the eye that provides improved illumination of ocular structures.

BACKGROUND OF THE INVENTION

Extraocular and intraocular slit beam illuminators are known and used in office and surgical settings for illuminating ocular structures, such as the cornea and lens surfaces and intraocular fluids and tissues including retina and vitreous. These structures, which are nearly-transparent, are difficult to distinguish using conventional illumination due to the small amount of light scatter which they produce when diffusely lit. The use of a slit-shaped beam allows selective, directed, and intense illumination of nearly-transparent tissues such that even a relatively small amount of scatter by such tissues allows them to be distinguished and otherwise observed or targeted for surgical modification or removal. The slit-illumination also provides a sense of depth, thickness, and three-dimensions to these transparent structures, especially when applied obliquely.

U.S. Pat. Nos. 6,080,143 and 5,630,809, commonly invented by the inventor of the present application and incorporated herein by reference, describe surgical illumination systems for providing illumination of intraocular target structures within an eye during surgical procedures for diagnosis or treatment of ocular conditions. The disclosed systems include an intraocular instrument having a distal end capable of insertion into the eye, the intraocular instrument having a light-conductor for transmitting a light beam, and a mask or other means for forming the light beam into a slit-shaped beam. The slit-shaped beam is emitted from the distal end of the instrument when the instrument is inserted into the eye such that intraocular slit-beam illumination of target structures is provided within the eye.

One drawback of conventional intraocular illuminators is that light directed into the eye from such illuminators is reflected off/from/through the patient's cornea/lens/retina or intraocular instruments, into the eyes of the surgeon, creating glare and lessening the quality/quantity of the illumination to target tissues.

OBJECTS AND SUMMARY OF THE INVENTION

It is an object of the invention to provide an improved intraocular probe for insertion into the eye that provides illumination of intraocular features. It is another object of the invention to provide an improved intraocular probe for insertion into the eye that provides therapeutic application of light.

In one embodiment the invention provides an intraocular light probe having a mask or shield affixed at its distal end thereof which forms a directed light beam for intraocular illumination of target tissues. The mask or shield serves to more fully focus, intensify and direct the beam toward the target tissues. The mask or shield also helps direct light away from other tissues and away from the eyes of the surgeon. The mask or shield thereby diminishes unwanted glare.

By placing a light probe beneath a surgical instrument such as a phacoemulsifier or vitrector, laser, cutting instrument (e.g., scissors or knife), forceps or probe/manipulator, whether as part of or separate from an infusion sleeve, a mask or shield effect is created. This has the same benefits of directing the beam toward target tissues, away from other tissues and away from the eyes of the surgeon.

The mask or shield is opaque or semi-opaque and made of a soft, semi-rigid or rigid material. If the mask or shield is semi-rigid, this allows the surgeon to bend the same into a shape which is appropriate for the particular intraocular application. The shield can be rigid enough to serve as the shaft of an instrument with a probe or manipulator at its distal tip. It may also be reflective on the side adjacent to the fiber bundle to help direct, magnify, and intensify the beam of light. The shape of the shield can be flat, curved or circular with an opening along one side. The mask/shield can be removed from the fiberoptic light for sterilization.

The device of the invention is preferably introduced into the eye via the primary, secondary, or side-port incision to provide intraocular cross-lighting of tissues during surgical procedures such as cataract surgery, corneal surgery, vitrectomy, intraocular lens implantation, refractive surgery, glaucoma surgery and vitreo/retinal surgery.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

DETAILED DESCRIPTION OF THE PREFERRED EMBODIMENT

Reference will now be made in detail to the preferred embodiments of the present invention, examples of which are illustrated in the accompanying drawings.

Figure 1:
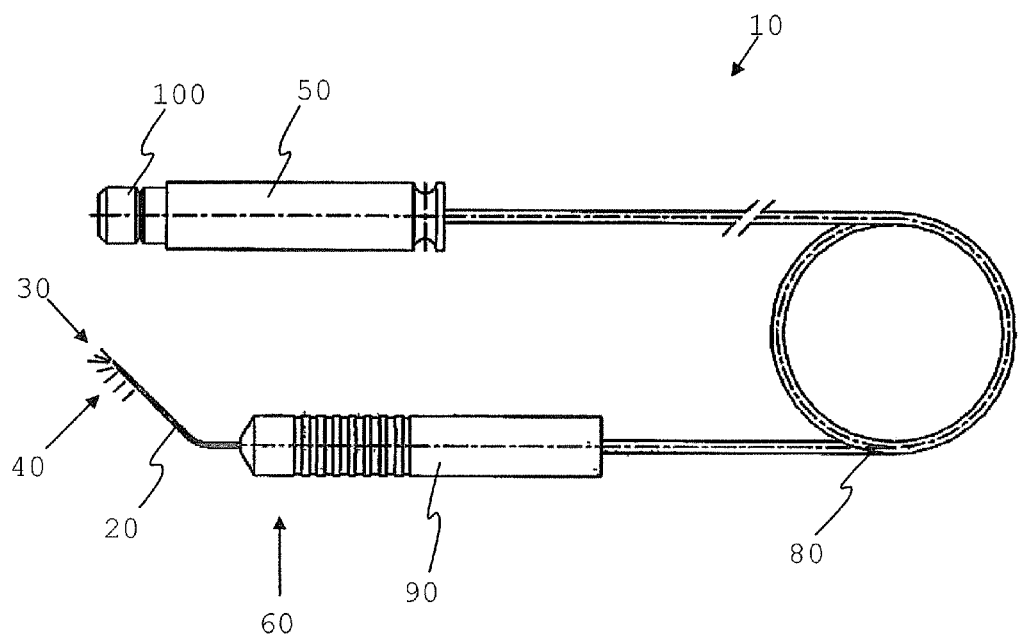
FIG. 1 is a side view illustrating a shielded intraocular illuminator in accordance with one embodiment of the invention.
Figure 2:
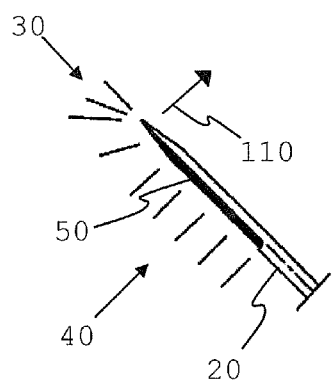
FIG. 2 is side view showing the detail of the mask or shield as illustrated in FIG. 1.

As shown in FIGS. 1 and 2, an intraocular light probe 10 has a mask or shield 20 affixed at its distal end 60 thereof which forms a directed light beam 30, 40 for intraocular illumination of, or application of therapeutic light to, target tissues. The mask or shield 20 is preferably opaque or semi-opaque, and may be constructed of metal, polymer, Teflon, or other suitable surgical-grade material. The mask or shield 20 may be constructed of a soft, semi-rigid or rigid material, but may be made rigid enough to serve as the shaft of an instrument with a probe or manipulator at its distal tip. The shape of the mask or shield can be flat, curved or circular, with an opening or aperture 50 along one side.

The opening or aperture 50 extends along at least a portion of the length of the mask or shield 20. The aperture 50 may be, e.g., 90 to 270 degrees in cross-section, and is preferably approximately 180 degrees in cross-section. The aperture 50 is preferably configured such that it permits light to be emitted from a distal portion of the mask or shield 20 in both a transverse (typically downward) and a longitudinal (typically forward) direction with respect to the length of the mask or shield 20. If the aperture is made to be narrow, e.g., 30 degrees or less, it will create a slit beam, which is more focused for intraocular illumination. While light 30, 40 is emitted in a transverse and a longitudinal direction, light is preferably shielded from being emitted in other directions by the mask or shield 20. If the mask or shield is shaped to have a concave curve, as shown in FIG. 2, light emitted from the aperture is more fully focused and intensified. The mask or shield 20 may also be made to be reflective on the side adjacent to the light guide 80 to help direct, magnify, and intensify the beam of light.

A connector 70 is provided for connecting the light probe 10 to a light source, and includes an appropriate fitting 100 for making the connection. The light source may be, e.g., a fiber optic light, lamp, laser, LED, or other light source appropriate for intraocular use, and is preferably variable in intensity. The connector 70 allows the light probe 10 to be disconnected from the light source for sterilization. A light guide 80 is provided for conducting light from the connector 70 to the mask or shield 20, and may be, e.g., an optical fiber, a bundle of optical fiber, flexible tubing, or a rigid light-conducting glass or polymer member. A handle 90 is provided for interconnecting the light guide 80 to the mask or shield 20, and may include ridges or other friction-increasing means for providing the surgeon with a firm grasp.

The mask or shield 20 serves to more fully focus, intensify and direct the beam toward the target tissues. The mask or shield 20 also helps direct light away from other tissues and away from the eyes of the surgeon, i.e., away from the direction generally indicated by arrow 110 on FIG. 2. The mask or shield thereby diminishes unwanted glare.

The distal end of the mask or shield 20 is preferably introduced into the eye via the primary, secondary, or side-port incision to provide intraocular cross-lighting of tissues during surgical procedures such as cataract surgery, corneal surgery, vitrectomy, intraocular lens implantation, refractive surgery, glaucoma surgery and vitreo/retinal surgery. By placing the mask or shield 20 beneath a surgical instrument such as a phacoemulsifier or vitrector, laser, cutting instrument (e.g., scissors or knife), forceps or probe/manipulator, a mask or shield effect is created. In this respect, the mask or shield 20 may be integrated with or separate from an infusion sleeve or other portion of such instruments. When integrated into or piggybacked with an intraocular instrument, the mask or shield 20 provides the benefits of directing the beam toward target tissues, away from other tissues and away from the eyes of the surgeon.

Figures 3A, 3B:
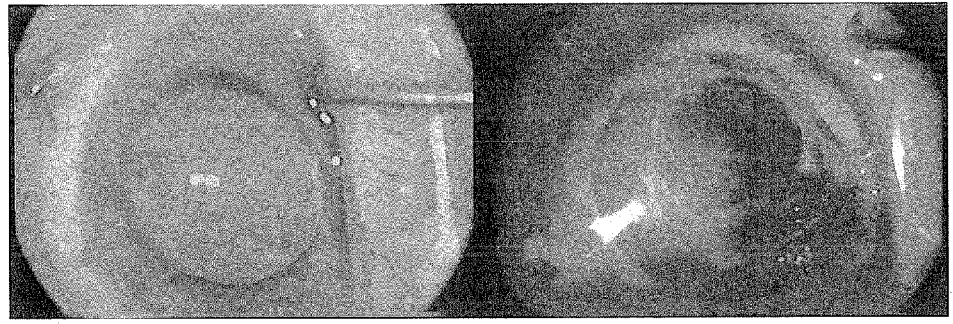
FIG. 3a shows a microscope view of an eye.
FIG. 3b shows a microscope view of an eye illuminated by a standard lightpipe bulb.

FIG. 3A shows a standard microscope or surgical view of an aphakic eye, where certain transparent tissues cannot be seen. FIG. 3b shows a standard microscope or surgical view of an aphakic eye using a standard lightpipe bulb—one will notice a great deal of glare off the cornea. FIGS. 3a and 3b show a cross-lighting demonstration of a posterior capsular opening with vitreous coming forward.

Figures 4A, 4B:
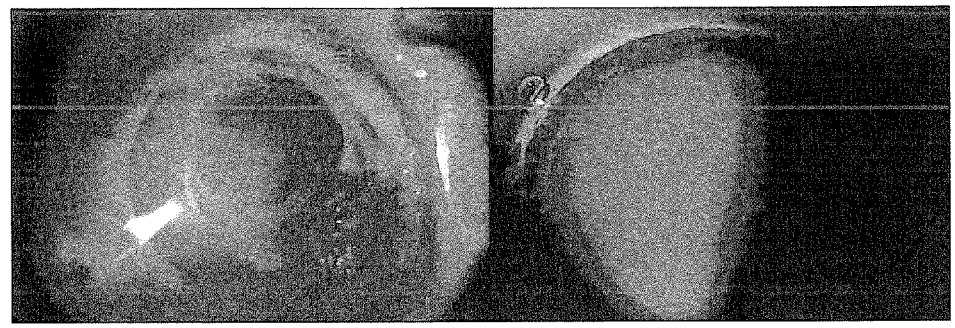
FIG. 4a shows a similar view as in FIG. 3b.
FIG. 4b shows a microscope view of an eye illuminated by a standard straight light pipe.

FIG. 4a shows a similar view as in FIG. 3b. Vitreous detail is appreciated in the drawing but a 25 ga bulb creates too much glare. In contrast, FIG. 4b shows a microscope view of an eye illuminated by a straight pipe beam giving too narrowed of a beam—it is too focused because the light is only coming from the tip. In FIG. 4b, pseudoexfoliation deposits are clearly seen but the beam is too narrow and overly focused using a straight 25 ga light pipe.

Figures 5A, 5B:
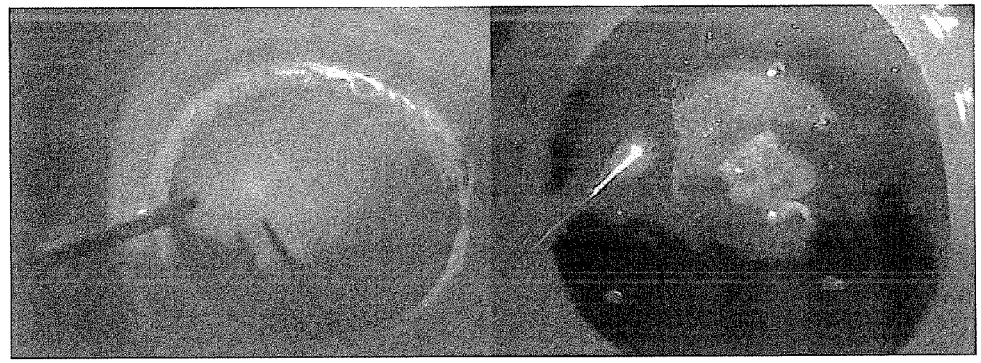
FIG. 5a shows a microscope view of an anterior capsule illuminated by a shielded beam according to one embodiment of the present invention, giving forward and downward illumination without glare.
FIG. 5b shows a microscope view of a posterior capsule illuminated by a shielded beam according to one embodiment of the present invention, giving forward and downward illumination without glare.

FIG. 5a shows a microscope view of an anterior capsule illuminated by a shielded beam according to one embodiment of the present invention, giving forward and downward illumination without glare. Capsular dyes can be avoided for the capsulorhexis in a white or black cataract. FIG. 5b shows a microscope view of a posterior capsule illuminated by a shielded beam according to one embodiment of the present invention, giving forward and downward illumination without glare. Illuminating this posterior capsular plaque demonstrates its three-dimensional characteristics.

Figure 6:
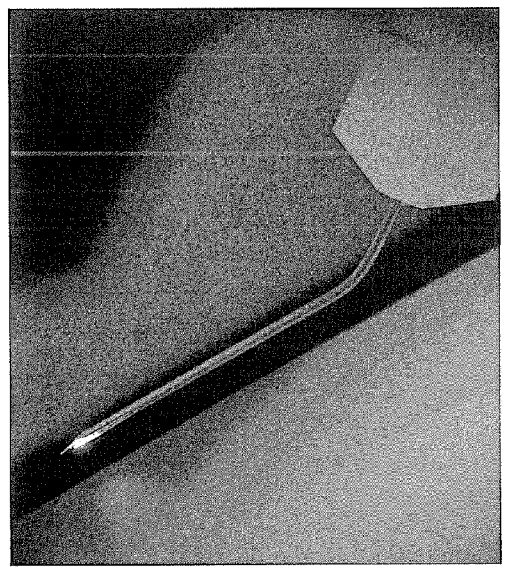
FIG. 6 shows a side view of a shielded pipe ("Connor Beam") according to one embodiment of the present invention.

FIG. 6 shows an actual shielded pipe according to one embodiment of the present invention.

An advantage of the present invention is the enhancement of visualization of those anterior segment tissues which are nearly invisible interoperatively. By taking advantage of smaller and brighter 25 ga fiberoptical lighting systems, the standard unenlarged anterior segment sideport incision offers access for direct illumination. This cross-lighting enables visualization of vitreous strands, posterior and anterior capsules, and corneal endothelium. Visualizing vitreous provides a more effective and efficient means of complete vitreous cleanup. Confirming the posterior capsular integrity aids in the decision of IOL placement. Cross-lighting the anterior capsule in opaque cataracts enhances visualization during the capsulorhexis without the use of dyes.

Improvements in fiberoptic systems now permit the use of bright 25 ga light pipes for smaller incisions. But current retinal 25 ga pipes in the anterior segment either create too much glare as in a bulbed tip (FIGS. 3a, 3b and 4a), or are too narrowed and overly focused as in a straight tip (FIG. 4b). The invention can provide a disposable 25 ga light pipe with an overlying shield to lessen glare. Its tapered tip allows for easy entry through an unenlarged sideport incision. Light is directed away from the surgeon's eyes and focused more toward the object of interest.

Interoperative cross-lighting for anterior segment surgery enables the surgeon to visualize transparent tissues with the same detail as the office slit lamp. This in turn provides more effective and efficient anterior segment surgery. This invention also benefits the posterior segment surgeon in the same way as set forth above, providing illumination of vitreous and retinal details without glare.

While the invention has been particularly shown and described with reference to a preferred embodiment thereof, it will be understood by those skilled in the art that various changes in form and details may be made therein without departing from the spirit and scope of the invention.

What is claimed is:

1. An intraocular probe for insertion into the eye to provide intraocular application of therapeutic light, comprising:
   a therapeutic light source for providing intraocular therapeutic light;
   a shield operably connected to said light source and having an aperture therein for directing said therapeutic light toward target tissues, said aperture being 180 degrees or less in cross-section, the shield shielding said therapeutic light from being directed toward other tissues and the eyes of a surgeon manipulating the light probe, whereby unwanted application of the light is diminished;
   wherein said aperture extends in a transverse direction and in a longitudinal direction with respect to a long axis of said shield and is configured to direct said therapeutic light in a forward and downward direction with respect to said long axis of said shield, and
   wherein said shield is configured to shield said therapeutic light from being emitted in other directions; wherein said shield has a tip that tapers with respect to said long axis of said shield, wherein said shield has a proximal end connected to said light source, and
   wherein said shield tapers at a distal end opposite from the end connected to said light source.

2. The intraocular probe according to claim 1, wherein the therapeutic light is laser light.

3. The intraocular light probe in accordance with claim 1, wherein said aperture is between 30 and 180 degrees in cross-section.

4. The intraocular light probe in accordance with claim 1, wherein an underside of the shield is polished or reflective to enhance light emitted from the probe.

5. The intraocular light probe in accordance with claim 1, wherein said shield is configured to be removable from said light source.

* * * * *